United States Patent [19]

Tolman et al.

[11] Patent Number: 4,488,991
[45] Date of Patent: Dec. 18, 1984

[54] BACTERIAL TOXOIDS AND GRAM-NEGATIVE IMMUNE GLOBULIN THEREFROM

[75] Inventors: Richard L. Tolman, Warren; Stephen Marburg, Metuchen, both of N.J.; Lynn T. Callahan, III, North Wales, Pa.

[73] Assignee: Merck & Co., Inc., Rahway, N.J.

[21] Appl. No.: 545,565

[22] Filed: Oct. 26, 1983

Related U.S. Application Data

[62] Division of Ser. No. 358,133, Mar. 15, 1982, Pat. No. 4,428,931.

[51] Int. Cl.$^3$ ...................... C07G 7/00; A61K 39/104
[52] U.S. Cl. ................................ 260/112 R; 424/92; 424/87; 536/26
[58] Field of Search ............................ 424/92; 536/26; 260/112 R

[56] References Cited

PUBLICATIONS

Chemical Abstracts, vol. 96, Abstract No. 3255e, 1982.
Proc. Natl. Aca. Sci. USA, vol. 80, pp. 2870–2873, May 1983, Biochemistry-Pseudomonas Exotoxin A: Toxoid Preparation by Photoaffinity Inactivation, S. Marburg, R. L. Tolman, and L. T. Callahan III.
Infection and Immunity, Mar. 1984, pp. 1019–1026, vol. 43, No. 3; Toxoids of Pseudomonas Aeruginosa Exotoxin-A: Photoaffinity Inactivation of Purified Toxin and Purified Toxin Derivatives-L. T. Callahan III, D. Martinez, S. Marburg, R. L. Tolman, and D. R. Galloway.
Proc. Natl. Acad. Sci. U.S.A., vol. 81, pp. 3307–3311, Jun. 1984.

*Primary Examiner*—Blondel Hazel
*Attorney, Agent, or Firm*—Gabriel Lopez; Richard A. Elder; Hesna J. Pfeiffer

[57] ABSTRACT

ADP-Ribosylating toxins are rendered enzymatically inactive by reactions with photolabile affinity reagents. The toxoids retain the antigenic and immunogenic properties of the original toxins. These bacterial toxoids can be used as immunogens to protect against the specific disease that the precursor toxins cause or, in the case of *P. aeruginosa*, the toxoid can be used in combination with *E. coli* J-5 vaccine to protect against gram-negative bacteremia in general.

3 Claims, No Drawings

BACTERIAL TOXOIDS AND GRAM-NEGATIVE IMMUNE GLOBULIN THEREFROM

This is a division of application Ser. No. 358,133, filed 3/15/82 now U.S. Pat. No. 4,428,931.

BACKGROUND

Inactivation of ADP-ribosylating toxins has been attempted by using cross-linking agents such as formaldehyde and glutaraldehyde. Cryz et al., "Effect of Formalin Toxoiding on *Pseudomonas aeruginosa* Toxin A: Biological, Chemical, and Immunochemical Studies", Infec. and Immun., 32, No. 2, 759–768, May 1981 describe such a toxoid. Two problems with some such toxoids have been reversion to the toxic form and loss of antigenicity and immunogenicity. The possibility of their reverting to the toxic state effectively precludes ever obtaining human antisera from such toxoids or their use as active vaccines.

SUMMARY OF THE INVENTION

It has now been found that ADP-ribosylating toxins such as exotoxin A from *P. aeruginosa* can be converted into toxoids with certain photolabile affinity reagents. The process is irreversible and the toxoid retains the antigenic and immunogenic properties of the parent toxin. Thus, the toxoid is useful as an immunogen against the specific disease caused by the parent toxin, or, in the case of *P. aeruginosa*, the toxoid can be combined with vaccines to bacterial endotoxins or antisera produced therefrom to offer a broader spectrum of protection against gram-negative bacteremia than heretofore possible.

An object of this invention is bacterial toxoids derived from ADP-ribosylating toxins, which are antigenic and immunogenic, and which do not spontaneously revert to the toxic state.

Another object is a process for producing such toxoids by reacting the corresponding toxins with certain photolabile affinity reagents.

A further object of this invention is the combination of the specific toxoid from *P. aeruginosa* with certain endotoxin vaccines. The vaccines could be used to induce antisera in mammals. The immune globulin obtained therefrom could be used to therapeutically treat acute gram-negative sepsis or used prophylactically and, in the case of *P. aeruginosa* bacteremia, to help prevent or cure this most devastating form of sepsis. Alternatively, the vaccines could be used to prevent these infections by active immunization.

DETAILED DESCRIPTION OF THE INVENTION

The ADP-ribosylating toxins which can be used in this invention are those which exhibit what is known in the art as ADP-ribosyltransferase activity and NAD-glycohydrolase activity. These include the exotoxin-A from *Pseudomonas aeruginosa*, the heat labile (LT) enterotoxin from *E. coli*, the cholera enterotoxin from *Vibrio cholerae*, and, in the case of gram-positive bacteria, the diphtheria exotoxin from *Corynebacterium diphtheriae*. All these toxins are known.

*P. aeruginosa* produces not only an endotoxin which is common to gram-negative bacteria, but also an exotoxin referred to as exotoxin-A. The exotoxin is a protein (mw approx. 70,000) which functions intracellularly as an enzyme with substrate specificity for NAD and causes its toxic effect by the ADP-ribosylation of Elongation Factor 2, thereby irreversibly preventing protein synthesis in the target cell. The toxoid of this invention has greatly reduced enzymatic activity (i.e, it is non-toxic) but is highly antigenic and immunogenic. The material is used to raise antibodies in mammals. The resulting immune plasma is used either as a monovalent or, in combination with immune plasma (or isolated antibodies therefrom) raised against generic antigens to endotoxin, as a divalent immunotherapeutic or prophylactic for gram-negative sepsis.

It is within the scope of this invention to enhance the immune response of the toxoids by binding said toxiods to a protein such as keyhole limpet hemocyanin.

In the process of this invention, the exotoxin is mixed with the photolabile affinity reagent, preferably in aqueous solution, in molar ratios ranging from 1:100 to 1:10,000. A ratio of 1:1300 has been found to work well. Degradation of the exotoxin and toxoid is minimized by maintaining the reagent vessel at about 0° C. and maintaining an inert atmosphere (e.g., $N_2$) in the vessel. The mixture is exposed to an effective amount of non-denaturing light, i.e., light containing an insubstantial amount of the U.V. portion of the spectrum. After activation by the light, the reacted material is purified, as by passage through an elution column.

The preferred photolabile affinity reagent is 8-azidoadenosine. Another within the scope of this invention is 8-azidoadenine, which has been found to be moderately effective. In the process of this invention, the 8-azidoadenine or 8-azidoadenosine, when irradiated, loses nitrogen in the form of $N_2$ and forms unstable nitrene intermediates (I). Said nitrenes then combine with the ADP-ribosylating toxins to form the novel toxoids: 8-adenylamino toxin and 8-adenosylamino toxin, respectively (II):

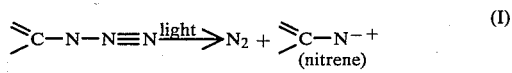

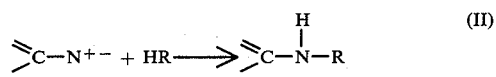

wherein RH is the ADP-ribosylating toxin. The complexes can, therefore, be described structurally as:

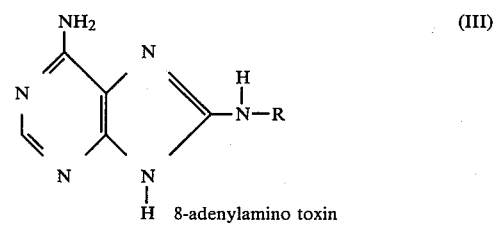

8-adenylamino toxin $$\text{8-adenosylamino toxin} \quad (IV)$$

[Structure: purine base with NH₂ group and N—R substituent at 8-position, connected to ribose with HO-CH₂, and OH OH groups]

wherein R is an ADP-ribosylating toxin radical. Thus, a toxoid of this invention derived from *P. aeruginosa* exotoxin A and 8-azidoadenine is 8-adenylamino *P. aeruginosa* exotoxin A; from 8-azidoadenosine it is 8-adenosylamino *P. aeruginosa* exotoxin A.

The invention is further defined by reference to the following preparations and examples, which are intended to be illustrative and not limiting.

The following procedure can be used to prepare, isolate, and purify *P. aeruginosa* exotoxin A.

PREPARATION 1

Purified Exotoxin A of *P. aeruginosa*

Step 1: DE-52 Preparation
  a. Two batches of excess DE-52 (Whatman DE-52 diethylaminoethyl cellulose, pre-swollen) (600–700 ml dry volume) were suspended in twice the volume of water and allowed to settle. The water was poured off and the DE-52 resuspended. With the second settling, a significant reduction in fines was noticed in the water. If this was not observed, it was repeated.
  b. The DE-52 batches were washed over coarse fritted glass filters with 3200 ml of 0.5N NaOH followed by 3200 ml H₂O, 3200 ml 0.5N HCl, 3200 ml H₂O, 3200 ml 0.5N NaOH and H₂O until the pH was below 8.
  c. The DE-52 was washed with several volumes of 0.01M NaCl 0.01M Tris buffer, pH 8.0.
  d. 100 ml of washed DE-52 was used to prepare a K 16/40 column, which was run at room temperature with a flow rate of 1.4 ml/min. The column was washed with 0.05M NaCl, 0.01M Tris pH 8.0 until it was equilibrated (1 to 2 days).

Step 2: Sephadex G-75 Column Preparation
  a. 136 g G-75 (Pharmacia) was rehydrated in 3 L 0.5M NaCl, 0.1M Tris, pH 8.0, boiled to degas and then cooled to 4° C. overnight.
  b. A Pharmacia K 50/100 column was packed with the G-75 (ca. 6h) at 4° C. and washed with buffer containing 0.02% w/v sodium azide.
  c. The column was checked with 40 mg blue dextran 2000 (Pharmacia) in 20 ml buffer at a flow rate of 0.5 ml/min collecting 7.6 ml fractions at 37 cm head pressure. The $V_o$ was 714 ml (40% of the bed volume) and the dilution factor was 5.3. The column was maintained at 4° C.

Step 3: Hydroxylappaltite (HTP) Column Preparation
  a. 120–150 ml dry volume of Hydroxylappaltite, (BIO-GEL HTP, Bio-Rad No. 130-0420) was suspended in twice the volume of 0.005M NaH₂PO₄, 0.1M NaCl pH 8.0 buffer.
  b. A Pharmacia K 26/40 column was packed with the HTP at a flow rate of 1.5 ml/min. at 4° C. and washed with buffer.

Step 4: Fermentation
Media - TSB-D (CM 679)
  a. Trypticase soy broth (Baltimore Biological Laboratory (BBL) No. 11768) was deferrated by mixing 1800 g TSB with 600 g Chelex 100, minus 400 mesh sodium form (Bio-Rad No. 142-2852), in 5400 ml water at room temperature for 5 to 6 hours (10X concentrate). It was then filtered through Whatman No. 1 filter paper and frozen until used.
  b. The chelated medium (a above) was diafiltered through an H10P10 hollow fiber cartridge in an Amicon Corp. DC-30 system. The concentrate was diluted in distilled water to 1X (60L) and diafiltered to yield 40 L TSB-D. The medium had a pH of 7.0 to 7.5; a chloride concentration of approximately 0.1M, and was sterilized by filtration (0.45 μm). The medium was stored at 4° C.
  c. On the day prior to fermentation, 2L of TSB-D was aseptically removed. To 1600 ml, 374 g monosodium glutamate and 400 ml glycerin were added, mixed at room temperature until dissolved, filtered through 0.45 μm filters and added as enriched medium to the fermentation vessel yielding a final concentration of 0.05M monosodium glutamate and 1.0% glycerin. The remaining 400 ml of non-enriched medium was saved for the seed flasks.

Tryptic Soy Agar Slants
  a. 40 g of TSA was allowed to swell in 1L water for 15 min. The mixture was boiled for one minute, aliquoted (8 ml per 1.2×12 cm screw-capped tubes) autoclaved 15 min, 121° C., 15 psi, then placed at a 15° angle to make long slants.

Growth
  a. One loopful each of the frozen stock of *P. aeruginosa* strain PA-103 (ATCC 29260)* was streaked onto four TSA (Tryptic soy agar, Difco) slants and incubated at 37° C. for 18 to 20 hours.
    *This strain was obtained from the ATCC, where it was deposited by P. V. Liu, University of Louisville, on Feb. 17, 1976. According to the ATCC, it is currently available and will continue to be so until at least A.D. 2002.
  b. The growth from all four slants was washed off with a total of 4 ml of medium. One ml of the suspension was used to inoculate each of four 250 ml baffled flasks containing 100 ml of non-enriched TSB-D. The cultures were incubated with shaking at 32°±1° C. and 250 oscillations per minute for 5 to 6 hours.
  c. All 400 ml of seed was used to inoculate 40 L of enriched TSB-D. The fermentation medium was saturated with O₂. Fermentation proceeded at 32°±1° C. with stirring while monitoring the pH (range 7.0–8.0) and optical density (to stationary phase growth) and maintaining the dissolved oxygen level at less than 25% of saturation for 18–24 hours.
  d. The bacteria were removed by centrifugation (20,000 rpm) in a model KII centrifuge (Electro-Neucleonics) and the supernatant fluid pre-filtered and filter sterilized (0.45 μm).

Step 5: Concentration
  a. Using an Amicon DC-10 hollow fiber system with an H10P10 cartridge the volume of supernatant fluid was reduced from 40 L to 3 to 4 L by diafiltration.
b. Cold water was added to the retentate to bring the level to 15 L and the pH was determined to be within 7.0 to 7.5 and the chloride concentration to be 0.02M. If the Cl$^-$ concentration was not sufficiently reduced, the diafiltration was continued until an acceptable concentration was obtained.

Step 6: DE-52 Batch Fractionation
a. 2L of washed DE-52 was added to the diluted retentate and mixed at room temperature for about 2 hours maintaining a pH of 8.0. When the pH was stable, the suspension was cooled to 4° C. and allowed to settle overnight.
b. Approximately 14 to 15 L of supernatant fluid was siphoned off and the cellulose was poured onto a 2.5 L fritted glass filter. The remaining fluid was removed under vacuum leaving the cellulose moist.
c. The cellulose was washed by filtration successively with 2.5L of 0.01M NaCl, 0.01M Tris pH 8.0; 0.05M NaCl, 0.01M Tris pH 8.0; and 0.25M NaCl, 0.01M Tris pH 8.0. The cellulose was discarded.
d. An enzyme assay, described below, was performed to confirm that the toxin was in the 0.25M NaCl fraction before proceeding with further fractionation.
e. The 0.25M NaCl active fraction was precipitated by adding solid ammonium sulfate at 70% (4° C.) saturation maintaining a pH of 8. The active fraction was held overnight for complete precipitation.

Step 7: G-75 Desalting
a. The precipitated fraction was mixed well and approximately ⅓ of the suspension was removed, holding the remainder at 4° C.
b. The aliquot was centrifuged at 16,000×g at 4° C. for 20 minutes (Sorvall RC5B, GSA rotor, 10,000 rpm) and the supernatant fluid was discarded.
c. The pellet was gently resuspended in 30 ml of 0.5M NaCl, 0.1M Tris, pH 8.0 buffer containing 0.02% Na azide. For clarification it was centrifuged at 17,000×g for 5 min. 4° C. It was then pre-filtered (0.8 μm) and then filter sterilized (0.45 μm).
d. The sample was chromatographed through the G-75 column at a flow rate of 1.5 ml/min and 7.5 ml fractions were collected. The fractions were assayed for toxin by countercurrent immunolectrophoresis (Hyland CEP Supply Package, Hyland, Lab) and the toxin-containing fractions were pooled. The immunoelectrophoresis was performed using monospecific equine antiserum to toxin (See Step 9-b).
e. The pool was precipitated with ammonium sulfate at 70% saturation, pH 8 and stored at 4° C.
f. Steps a to e were repeated twice more with the remaining DE-52 fraction. The precipitates were then pooled.

Step 8: HTP Fractionation
a. The G-75 precipitates were collected by centrifugation as before.
b. The pellet was gently dissolved in 20 ml 0.005M NaH$_2$PO$_4$, 0.1M NaCl pH 7.0 starting buffer and dialyzed against 2L of buffer at 4° C. overnight.
c. The sample was run through an Hydroxylappaltite Bio-Gel HTP (Bio-Rad) column at a flow rate of 1.5 ml/min and chased with 3 bed voluxes of 0.01M NaH$_2$PO$_4$, 0.1M NaCl pH 7.0. The optical density (O.D.) at 280 nm was monitored on a Beckman Spectrophotoxeter model 26. The non-adsorbing material was completely eluted from the column before proceeding to the next step.
d. The buffer was changed to 0.06M NaH$_2$PO$_4$, 0.1M NaCl pH 7.0 and 7 ml fractions were collected. The O.D. peak was assayed by CIE.
e. The toxin fraction was pooled and precipitated by dialysis against saturated ammonium sulfate at 4° C. overnight.

Step 9: DE-52 Gradient Fractionation
a. The precipitate was collected by centrifugation at 12,000×g for 10 minutes at 4° C. (Sorvall SS34 rotor, 10,000 rpm). It was then gently resuspended in 5 ml 0.05 M NaCl, 0.01M Tris pH 8.0 (starting buffer) and dialyzed against 1 L of the starting buffer twice at 20° C. for 18 to 24 hours.
b. DE-52 chromatography was performed with a linear 1 L gradient of 0.05M to 0.5M NaCl in 0.01M Tris pH 8.0. Two and one half ml fractions were collected at a flow rate of 1.4 ml/min. The toxin peak ($O.D._{280}$ nm) was eluted at or about 0.15M $Cl^-$ and was assayed by countercurrent immunolectrophoresis (CIE) with monospecific equine antiserum at 30 mA for 60 minutes to determine the fractions to be pooled.

c. A determination was made of the pool $O.D._{280}$ nm and the protein concentration was calculated by the following equation: [1% solution $O.D._{280}$ nm=18.5]

d. Aliquots of 2.5 ml/6ml vial were made and stored at −70° C.

The purified exotoxin A was then used to prepare the P. aeruginosa toxoid of Example 1.

EXAMPLE 1

Preparation of *P. Aeruginosa* Toxoid 12 mg of 8-azidoadenosine (prepared according to Holmes et al., J. Am. Chem. Soc., 87, 1772 (1965)) was covered with 10 ml of pH 7.4 buffer (9.5 mM phosphate, 140 mM NaCl) and shaken until most dissolved, i.e., forming a saturated solution. The suspension was filtered through a sintered glass filter and the concentration of the filtrate determined by ultraviolet spectroscopy. The filtrate was diluted 1 to 50 with the above pH 7.4 phosphate buffer and the absorption, $\lambda_{max}$282, $\epsilon$=14,500 determined. The concentration of 8-azidoadenosine was $2.9\times10^{-3}$M. 7.5 ml of this solution was mixed with 7.5 ml of *Pseudomonas aeruginosa* exotoxin A (150 μg/ml, 1125 μg total) from Preparation 1. The final molar ratio of azido compound to toxin was 1300:1.

This solution was charged (in 2×7.5 ml batches) into a 12 ml Pyrex reactor surrounded by a jacket through which ice water was pumped. Prior to irradiation, the reactor was stoppered with a serum cap through which a hypodermic needle was inserted, and the vessel was then alternately evacuated and flushed with nitrogen. Photolysis was effected by a 450W Hanovia medium pressure lamp (6794 0360) placed 4 inches from the reactor for 6 minutes with cooling.

The solution was then desalted by passage through six Sephadex PD 10 columns (addition in 2.5 ml batches and elution with 3.5 ml of pH 7.4 buffer). The eluates were assayed by High Performance Liquid Chromatography on a 60 cm Toya Soda molecular sieve column. The material (8-adenosylamino *P. aeruginosa* exotoxin A) was found to be a single peak at about 68,000 Daltons and corresponded to about 55±10 μg/ml as determined by peak area (using pure toxin as standard). A similar value was determined using a colormetric protein assay (Biorad).

EXAMPLE 2

Toxicity Assays

Exotoxoid prepared as in Example 1 is compared to exotoxin A with regard to cytotoxicity, guinea pig skin reaction, and enzyxe activity.

Mouse fibroblasts or L cells from a cell line continuously maintained in our laboratory were used as target cells in an in vitro microcytotoxicity assay. When these L cells, growing in microculture, are exposed to nanogram amounts of purified exotoxin, they show microscopic evidence of cell death (e.g., loss of normal architecture, "balling up", and loss of adherence to plastic surfaces). These visually observed cytotoxic changes correspond to and can be quantified by the inhibition of [$^3$H] thymidine incorporation by the toxin-exposed cultures. The titer at 50% inhibition is then calculated by graphing the percent inhibition as a function of the log of the dilution of toxin.

The guinea pig skin test is perfomed by intradermal injection of 0.1 ml of the test compound at two sites on shaved and depilated adult Hartley white guinea pigs. Three days after injection, the areas of reaction sites are measured in mm$^2$.

The enzyxe assay quantifies the degree of ADP-ribosylation of EF-2 by measuring the incorporation of the tracer (adenine-$^{14}$C)-NAD into TCA precipitable product. Under the assay conditions, the following reaction occurs:

$$\text{EF-2} + (^{14}\text{C})\text{-NAD} \underset{}{\overset{\text{sample}}{\rightleftarrows}} \text{ADP-ribose EF-2 (product)} + \text{nicotinamide} + \text{H}^+$$

As the presence of exotoxin favors ADP-ribosylation of EF-2, the amount of radioactivity (counts per minute minus background noise) in the precipitable product is a measure of the amount of toxin in the sample. If the amount of toxin is held constant, then the amount of radioactivity incorporated into EF-2 is a function of time. Assaying at various time intervals reveals the velocity of the reaction.

Samples of exotoxoid, prepared as in Example 1, and exotoxin A were assayed as above and the following data were obtained:

TABLE 2-1

Cytotoxicity, Skin Reaction, and Enzyme Activity Assays

| Sample | Cyto. $ID_{50}$(ng)/$10^3$ Cells | Skin React. Area (mm$^2$) | Enzyme Velocity nM ADP-ribose EF-2/min/ng protein |
|---|---|---|---|
| Toxin | 4 | 153 | 155 |
| Toxoid | 887 | 7 | 9 |
| Reduction | 99% | 95% | 94% |

EXAMPLE 3

Antigenicity Assay

Samples of exotoxin (Preparation 1) and exotoxoid (Example 1) were tested for antigenicity using monospecific equine antiserum. The following data were obtained.

TABLE 3-1

Rocket Immunoelectrophoresis

| | Peak Hgt. of Rockets (mm) Avg. of 2 rockets |
|---|---|
| Toxin (Prep. 1) 150 ng | 36.5 |
| Toxoid (Ex. 1) 150 ng | 36.0 |

From these data, it is concluded that the toxoid retains approximately 100% of the original toxin's antigenicity.

EXAMPLE 4

Potency Assay (Antibody Response)

Mice were vaccinated i.p. on day 1 with 5 μg alum absorbed toxoid (alum-toxoid); on day 7 with 5 μg alum-toxoid i.p.; and on day 21 with 5 μg aqueous-toxoid i.v. On day 25, 32 immunized mice were bled and antitoxin titers were determined by ELISA assay.

Sera were dilated 1:40, 1:160, and 1:640. The following definitions were used in Table 4-1.

| | ELISA Optical Density (O.D.) at 405 nm |
|---|---|
| Negative Response: | $<2 \times$ B kg.* at 1:40 |
| Low Response: | $>2 \times$ B kg. at 1:40, and $\leqq 2 \times$ B kg. at 1:160 |
| Medium Response: | $>2 \times$ B kg. at 1:40, and $>2 \times$ B kg. at 1:160, but $<4 \times$ B kg. at 1:640 |
| High Response: | $\geqq 4 \times$ B kg. at 1:640 |

*B kg. = Background O.D. of samples not containing serum (i.e. serum controls).

TABLE 4-1

ELISA Results of Toxoid Immunized Mice

| Type of Response | % of Mice Tested |
|---|---|
| Negative | 12.5 |
| Low | 6.25 |
| Medium | 59.4 |
| High | 21.8 |

Based on these data, it is concluded that there was a total of approximately 87% antibody responders to vaccination with as little as a 15 μg dosage.

EXAMPLE 5

Toxoid Stability

To demonstrate that the toxoid does not revert to the toxic state, toxoid (Ex. 1) and toxin (Prep. 1) were dialyzed exhaustively against PBS for 1 week at RT. and then the toxoid was allowed to remain for an additional three weeks at 4° C. Samples were removed and tested for enzyme activity and the following data were obtained.

TABLE 5-1

| | Enzyme Activity (cpm/μg protein) |
|---|---|
| Toxin | 947 |
| Toxoid (Day 0) | 90 |
| Toxoid (1 Wk.) | 91 |
| Toxoid (1 Mo.) | 92 |

Based on these data, it is concluded that the toxoid remains stable and does not revert to toxin over at least a 1-month period.

Following the procedure of Example 1, toxoids may be prepared from other ADP-ribosylating toxins such as those from *E. coli, Vibrio cholerae,* and *Corynebacterium diphtheriae.*

The toxoids of this invention may be used in mammalian species for either active or passive immunization prophylactically or therapeutically against disease caused by the corresponding organism. Passive vaccination can be accomplished by injecting either whole antiserum or immune globulin obtained from mammals previously vaccinated with the toxoid, with or without a pharmaceutically acceptable carrier. Such globulin is obtained by standard techniques from whole antiserum.

In a preferred embodiment of this invention, the exotoxoid of Example 1 is used in combination with a vaccine, which combination offers much broader protection against gram-negative bacteremia. The second component is used to raise antibodies against gram-negative bacterial endotoxins. The preferred organisms are *Salmonella minnesota* Re 595 and the J-5 mutant of *E. coli* 0111 B 4. These are preferred as they appear to raise antibodies against core glycolipids common to gram-negative endotoxin and, therefore, offer a broader spectrum of protection than organisms which would merely raise antibodies specific to themselves. The use of J-5 is taught in Braude et al., Antiserum treatment of gram-negative bacteremia, Schweiz. Med. Wschr. 108, No. 48, pp. 1872–1876 (1978). An unrestricted permanent deposit of the J-5 *E. coli* organism used herein was made with the American Type Culture Collection on Jan. 21, 1982 under accession No. ATCC 39041. Although other *E. coli* strains may be used in the practice of this invention, ATCC 39041 is preferred.

In the practice of this preferred embodiment, antisera are raised as taught by Braude et al. or by Ziegler et al., *Trans. Assoc. of Amer. Phys., XCI,* 253–258 (1978). These antisera are then combined with toxoid antisera to form a bivalent immuno-therapeutic or prophylactic. Alternatively, and preferably, the immuno-globulins of these antisera are used instead of the whole antisera.

Therefore, the toxoids of this invention are used in injectable form for active, prophylactic immunization of mammalian species against disease caused by the corresponding organism. Alternatively, immunoglobulin derived from said toxoids may be used for passive immunization, prophylactically or therapeutically. When *P. aeruginosa* toxoid is used, it is combined with antibodies raised against bacterial endotoxins. When the *P. aeruginosa* toxoid is combined with gram-negative bacterial endotoxin vaccine or derivatives thereof such as antisera or immunoglobulin, the injectable form offers much broader protection against gram-negative bacteremia. By the injectable form of the toxoids of this invention is xeant an effective amount of said toxoids, antisera derived from said toxoids, gammaglobulin or other antibody-containing fractions of said antisera, said toxoids, antisera, or fractions being used singly or in combination with a gram-negative bacterial endotoxin vaccine, antisera obtained from said endotoxin vaccine, or gamma globulin or other antibody-containing fractions of said antisera, said injectable form further optionally comprising a pharmaceutically acceptable carrier, such as aseptic saline water. The use of an acceptable adjuvant (e.g., alum) is also intended to be within the scope of this invention. In non-human mammals, a complete or incomplete adjuvant (e.g., Freund's) can be used.

Although the toxoids of this invention have not been tested in humans, the mouse data of Example 4 suggest that at least 5–25 $\mu$g toxoid are effective to induce an antibody response in mammals, i.e., that such an amount is an effective amount for immunization or to produce antisera in volunteer subjects. For the production of antisera on a long term basis, booster injections at 2-week intervals may be necessary. Likewise, from the data of Example 6, it is calculated that at least about 90 ml of human antiserum raised against bacterial endotoxins having a minimum PHA (passive hemagglutination assay) titer of 1:32 is required to protect a 70 kg human (1.25 ml or greater per kg of body weight) against gram-negative bacterial endotoxins.

PREPARATION 2

Mice Immunosuppression

The mice used in Example 4 were also used in Example 6. They were immunosuppressed after developing antibodies to toxin in order to obtain a model which better resembles a clinically relevant situation.

Caesarian-derived, barrier-sustained, outbred albino (CFl) mice from Charles River were used. Mice were 5.5 to 7 weeks old (20 to 24 grams) at the time of challenge.

Mice were immunosuppressed one day before challenge with cyclophosphamide (CYTOXAN, Meade Johnson & Co.). The Cytoxan was disolved in sterile, pyrogen-free, distilled water at a concentration of 20 mg/ml (Cytoxan also contains NaCl for isotonicity). The concentration of the solution was adjusted with sterile, pyrogen-free phosphate-buffered saline to deliver by intraperitioneal injection the appropriate dose (400 mg/kg) in 1 ml.

PREPARATION 3

*P. Aeruginosa* Challenge

Frozen bacterial stock of a clinical isolate of *P. aeruginosa* was thawed the day before the challenge, inoculated on a trypticase soy agar slant, and incubated at 37° C. overnight. The next day the bacteria were suspended in 2.5 ml of phosphate-buffered saline inoculated into 100 ml of trypticase soy broth, and incubated at 37° C. in a shaker-incubator. When the bacteria reached mid-logarithmic growth, they were washed 3 times in phosphate-buffered saline, and resuspended in PBS at a concentration of $7 \times 10^6$ bacteria/ml. The mice were given 0.1 ml of the suspension intraperitoneally (i.e., $LD_{95}$ dose).

EXAMPLE 6

Mice Immunization

In order to demonstrate the immunogenicity of toxoid, prepared as in Example 1, mice with antibody titer distributions listed in Table 4-1 were immunosuppressed and challenged with *P. aerugina* by intraperitoneal injection (Prep. 3). Positive and negative controls were used as well as treatment with placebos. The improved efficacy achieved by combining the said toxoid active immunization and passive immunization with antisera obtained from J-5 *E. coli*-vaccinated human volunteers was also demonstrated. The antisera were obtained following the procedure described in Ziegler et al., *Trans. Assoc. of Amer. Phys., XCI,* 253–258 (1978). The J-5 *E. Coli* organism used is now on deposit with the American Type Culture Collection under Accession No. ATCC 39041. The data of Table 6-1 were obtained.

These data show that:
(1) Untreated, challenged animals die quickly (VI).
(2) Untreated, unchallenged animals die later of natural infections (V).
(3) J-5 antiserum alone offers some protection (III vs. VI).
(4) The combination of toxoid treatment and passive J-5 antiserum treatment is efficacious (I vs. II).
(5) Because of 4, the toxoid is immunogenic.
(6) Combined treatment also protects against natural infections (I vs. V).

TABLE 6-1

Protection Against *P. aeruginosa* Infections In Mouse Immunosuppression Model

| | | No. of Deaths | | | | | Day 5 | |
|---|---|---|---|---|---|---|---|---|
| | Treatment | Day 1 | Day 2 | Day 3 | Day 4 | Day 5 | Dead/Total | % Survival |
| I. | Toxoid Immune[A] + Passive Post.J-5[B] | 0 | 1 | 0 | 2 | 0 | 3/32 | 91 |
| II. | Toxoid Immune + Passive Pre-J-5 | 0 | 0 | 1 | 5 | 9 | 15/31 | 52 |
| III. | Placebo + Passive Post-J-5 | 0 | 0 | 1 | 3 | 10 | 14/33 | 58 |
| IV. | Placebo + Passive Pre-J-5 | 0 | 0 | 2 | 3 | 7 | 12/32 | 63 |
| V. | No Treatment + No Challenge | 0 | 0 | 0 | 2 | 10 | 12/39 | 69 |
| VI. | No Treatment + Challenge | 25 | 10 | 2 | 0 | 0 | 37/39 | 5 |

[A]Animal immunized per Ex. 4; challenged on Day 29 post initial immunization day.
[B]Equivalent to 25 μl of human volunteer antiserum having a PHA titer of 1:32 and given i.p. 4 hours prior to challenge.

What is claimed is:

1. A process for preparing toxoids which comprises:
   (1) mixing and ADP-ribosylating toxin with a photolabile affinity reagent selected from the group consisting of 8-azidoadenosine and 8-azidoadenine, at about 0° C. under an inert atmosphere, and
   (2) exposing the mixture of step 1 to an effective amount of nondenaturing light.

2. The process of claim 1 wherein the toxin is *P. aeruginosa* exotoxin-A, the photolabile affinity reagent is 8-azidoadenosine and the molar ratio of exotoxin to photolabile affinity reagent ranges from 1:100 to 1:10,000.

3. The process of claim 1, also comprising (3) desalting the the toxoid product of step 2.

* * * * *